United States Patent [19]

Sojka

[11] Patent Number: 5,389,726
[45] Date of Patent: Feb. 14, 1995

[54] NAIL LACQUER PRIMARY FILM FORMING RESIN

[75] Inventor: Milan F. Sojka, Midland, Mich.

[73] Assignee: Dow Corning Corporation, Midland, Mich.

[21] Appl. No.: 270,289

[22] Filed: Jul. 5, 1994

Related U.S. Application Data

[62] Division of Ser. No. 238,607, May 5, 1994.

[51] Int. Cl.6 .............................................. C08L 83/00
[52] U.S. Cl. .................................. 525/100; 525/288; 525/292
[58] Field of Search ....................... 525/100, 288, 292

[56] References Cited

U.S. PATENT DOCUMENTS

| | | | |
|---|---|---|---|
| 4,288,356 | 9/1981 | Huebner et al. | 525/100 |
| 4,962,156 | 10/1990 | Shinjo et al. | 525/100 |
| 5,153,268 | 10/1992 | Lagow et al. | 525/288 |
| 5,252,445 | 10/1993 | Timmerman et al. | 525/191 |

*Primary Examiner*—John C. Bleutge
*Assistant Examiner*—Mark D. Sweet
*Attorney, Agent, or Firm*—James L. DeCesare

[57] ABSTRACT

An improved nail lacquer containing a film forming resin, a plasticizer, and a solvent. The improvement resides in utilizing as the film forming resin a blend of: (i) a graft copolymer having a main backbone chain of acrylic ester units and methacrylic ester units, with the main backbone chain having grafted thereto pendant trialkoxysilyl groups and pendant ethylene glycol dimethacrylate groups; and (ii) a silsesquioxane resin containing $RSiO_{3/2}$ units and $\equiv SiOH$ units in which R is an alkyl group or an aryl group. In an alternate form of the invention, the film forming resin is not a blend, but an improved type of graft copolymer containing, in addition to pendant trialkoxysilyl groups, pendant vinylbenzyl chloride groups.

8 Claims, No Drawings

NAIL LACQUER PRIMARY FILM FORMING RESIN

This is a divisional of copending application Ser. No. 8/238,607, filed on May 5, 1994.

BACKGROUND OF THE INVENTION

This invention relates to a primary film forming resin for nail lacquers and nail enamel formulations and more particularly is directed to a grafted polymeric film forming resin for nail polish which will function as a replacement for nitrocellulose.

Nail lacquers and enamels typically contain several ingredients among which are a primary film former, secondary film formers, plasticizers, solvents, colorants, and fillers. In the past, nitrocellulose has been the primary film former employed in the majority of nail polish formulations but it suffers from the disadvantages that it is explosive; it tends to discolor as a function of time rendering it aesthetically displeasing; and it is prone to undergo sharp changes in viscosity which make application difficult. Thus a need exists in the nail lacquer arts For an improved primary film forming material.

Unlike copolymers having a linear arrangement of sequences such as -AAABBB- and -ABABAB-, graft copolymers are polymers in which the molecules are characterized by a main backbone chain to which side chains containing different atomic constituents are attached at various points along the main chain. For example a graft copolymer can be represented by the structure

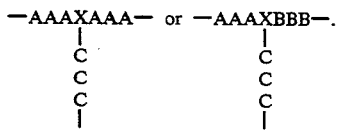

A and B are referred to as the main chain or backbone, the sequence of C units is the side chain or graft, and X is the unit in the backbone to which the graft is attached.

Nail lacquers containing graft copolymers are not new. For example, in U.S. Pat. No. 5,153,268 issued Oct. 6, 1992, there is described a nail lacquer formulation containing as the film forming resin a graft copolymer having a main backbone chain of acrylic ester monomer units and methacrylic ester monomer units. Grafted to the main backbone chain are side chain units of carboxyl groups and side chain units of trialkoxysilyl groups.

The present invention is an improvement in graft copolymers and nail lacquers in accordance with the '268 patent. Accordingly, in the present invention ethylene glycol dimethacrylate side chain units are grafted to the main backbone chain instead of carboxyl groups, and the resulting graft copolymer is cold blended with q silsesquioxane resin. The blended material is useful as a film forming resin in nail lacquer applications. It possesses improved chip resistance, wearability, hardness, and gloss. The graft copolymer provides improved adhesion and the silsesquioxane resin provides improved hardness for the nail lacquer system.

In an alternate embodiment of the invention, improved nail lacquer film forming resins are obtained by grafting to the main backbone chain, in addition to the trialkoxysilyl groups, side chain units of vinylbenzyl chloride, instead of carboxyl groups as in the '268 patent. Such film forming resins in accordance with this alternate embodiment have been found to possess significantly better adhesion characteristics than the carboxyl group containing film forming resins of the '268 patent.

SUMMARY OF THE INVENTION

The invention is directed to a graft copolymer which has a main backbone chain of acrylic ester monomer units and methacrylic ester monomer units. The main backbone chain has grafted thereto side chain units of ethylene glycol dimethacrylate groups and side chain units of trialkoxysilyl groups. The copolymer is then cold blended with a silsesquioxane resin.

The invention is also directed to a nail lacquer which includes a film forming resin, a plasticizer and a solvent. The improvement in accordance with the present invention relates to the utilization as the film forming resin of the nail lacquer the graft copolymer blend noted above.

Nail coat compositions containing the novel film forming resins and blends of the present invention have been found to provide improved wear resistance which is a highly desirable and sought after factor in the nail enamel market.

In an alternate embodiment, vinylbenzyl chloride groups are grafted to the main backbone chain. These and other features, objects and advantages of the herein described present invention will become more apparent when considered in light of the following detailed description.

DETAILED DESCRIPTION OF THE INVENTION

Nail lacquer formulations exhibiting improved wear resistance are provided herein by incorporating into nail care compositions as the film forming ingredient a graft copolymer. The graft copolymer in accordance with the present invention includes a main backbone chain of acrylic ester monomer units and methacrylic ester monomer units. In addition the main backbone chain has grafted thereto side chain units of ethylene glycol dimethacrylate groups and side chain units of trialkoxysilyl groups. The graft polymers of the present invention can be represented by the segment structure

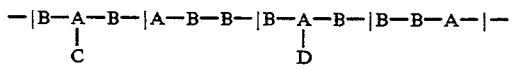

in which A represents an acrylate monomer unit, B represents a methacrylate monomer unit, C represents an ethylene glycol dimethacrylate group and D represents a trialkoxysilyl group.

This random grafted copolymer contains in a typical segment of one hundred A and B units, thirty-three A units and sixty-seven B units. However in such a one hundred unit segment there is only one C unit and one D unit. The C and D units graft to only the A units. In other words, of one hundred "mer" units of the polymer there are sixty-seven B units, thirty-one A units, one A unit that has a C unit grafted thereto, and one A unit that has a D unit grafted thereto. The distribution of the "mer" units is random.

The acrylic ester monomer has the formula $CH_2=CHCOOR$ in which R is preferably an alkyl group having from one to sixteen carbon atoms. The methacrylic ester monomer has the formula $CH_2=C(CH_3)COOR'$ in which R' is an preferably an alkyl group having one to fourteen carbon atoms. Most referred are main backbone chain copolymers in which the acrylic ester monomer is butyl acrylate and the methacrylic ester monomer is methyl methacrylate.

The ethylene glycol dimethyacrylate graft is formed by reacting the main backbone chain copolymer with ethylene glycol dimethacrylate in the presence of a free radical initiator. The trialkoxysilyl graft is formed by reacting the main backbone chain copolymer with an acrylate or a methacrylate functional silane monomer in the presence of a free radical initiator. The grafts are formed by reacting the copolymer with ethylene glycol dimethacrylate and the silane monomer in the presence of a free radical initiator. The silane monomer is preferably 3-methacryloxypropyltrimethoxysilane although there may also be employed methacryloxypropenyltrimethoxysilane, 3-methacryloxypropyltris(methoxyethoxy)silane, and 3-acryloxypropyltrimethoxysilane.

While the most preferred monomers for the backbone chain copolymer are butyl acrylate and methyl methacrylate, other combinations of acrylates and methacrylates may be employed such as methyl, ethyl, propyl, pentyl, hexyl, octyl, nonyl, decyl, dodecyl, tetradecyl and hexadecyl acrylates; and ethyl, propyl, isopropyl, n-butyl, isobutyl, sec-butyl, t-butyl, n-hexyl, n-octyl, isooctyl, 2-ethylhexyl, n-decyl and tetradecyl methacrylates.

A particularly distinct advantage of the present invention is that there is produced a material which contains less than about ten parts per million of residual monomer. Thus a practically monomer free product is produced by virtue of the fact that any residual monomer is grafted to the polymer.

The improved film forming nail lacquer resins of the present invention are made by mixing together an organic acrylate monomer, an organic methacrylate monomer, a free radical initiator, and a solvent ester such as ethyl acetate. The solution is heated for six to twelve hours at fifty to one hundred degrees Centigrade, accompanied with stirring at a rate of one hundred to one thousand revolutions per minute. There is added to the solution a trialkoxysilyl acrylate monomer and a free radical initiator at room temperature. The concentration of the trialkoxysilyl acrylate monomer relative to the acrylate/methacrylate copolymer can be from 0.1 to 10.0 percent, but is preferably about three percent. This is followed by addition to the solution of an ethylene glycol dimethacrylate monomer together with a free radical initiator at room temperature. The concentration of the ethylene glycol dimethacrylate monomer relative to the acrylate/methacrylate copolymer can also be from 0.1 to 10.0 percent, but is preferably about 1.5 percent. A final product, in the form of a solution containing ten to fifty percent by weight, preferably thirty percent by weight of the graft copolymer, is obtained by heating the solution for three to six hours at a temperature of fifty to one hundred degrees Centigrade.

The graft copolymer solution is cold blended with a solution containing a silsesquioxane resin in an ester solvent such as ethyl acetate. The concentration of the silsesquioxane resin in the solution can be from ten to fifty percent, but is preferably about thirty percent, The solutions of the graft copolymer and the silsesquioxane resin are blended in a ratio of ten to fifty parts by weight of the graft copolymer solution and fifty to ninety parts by weight of the silsesquioxane resin solution.

The silicone resin used in accordance with the present invention is a silsesquioxane resin containing $RSiO_{3/2}$ units and $\equiv SiOH$ units, in which R is an alkyl or aryl group such as methyl, ethyl, propyl, butyl, phenyl, or benzyl. Such resins and methods for their preparation are known in the apt, and are shown and described for example in U.S. Pat. No. 3,264,260 issued Aug. 2, 1966, and U.S. Pat. No. 5,075,103 issued Dec. 24, 1991.

One representative silicone resin and a particularly preferred silsesquioxane resin is a material having the formula $(PhSiO_{3/2})_x(PrSiO_{3/2})_yOH$ in which Ph is phenyl, Pr is propyl, and the ratio of x:y is 7:3. Another representative silsesquioxane resin is a material having the formula $(PhSiO_{2/2})_a(MePhSiO_{2/2})_b(PhSiO_{3/2})_c(MeSiO_{3/2})_dOH$ in which Ph is phenyl, Me is methyl, and the ratio of the integers a:b:c:d is 10:5:40:45, respectively.

Suitable free radical initiators which may be employed include organic peroxides such as diacyl peroxides, peroxyesters, dialkyl peroxides, and peroxydicarbonates; and azo compounds. These initiators are known in the art and representative initiator compounds of the foregoing categories include dibenzoyl peroxide, t-butyl peroctoate, dicumyl peroxide, diisopropyl peroxydicarbonate, and 2,2'-azobis(isobutyronitrile), respectively.

In the case of the alternate embodiment of the invention, the same procedure is used, except that vinylbenzyl chloride is employed as the monomer for grafting instead of ethylene glycol dimethacrylate. In addition, the graft copolymer containing the vinylbenzyl chloride grafted units is used without blending with the silsesquioxane resin.

The following examples are set forth in order to further illustrate the concepts of the present invention.

EXAMPLE I

Into a three neck reaction flask containing 700 grams of ethyl acetate solvent and three grams of t-butyl peroctoate free radical initiator, there was added and dissolved 204.63 grams of butyl acrylate and 81.18 grams of methyl methacrylate. The solution was purged with argon for fifteen minutes. While stirring and maintaining an argon blanket, the system was heated to sixty degrees Centigrade for one hour, and then heated to reflux at eighty degrees Centigrade for ten hours. After cooling to room temperature, there was added 4.86 grams of ethylene glycol dimethacrylate and three grams of t-butylperoctoate initiator. The system was purged with argon for fifteen minutes, an argon blanket was established, and the polymerization was allowed to proceed for five hours at eighty degrees Centigrade. The flask was allowed to cool to room temperature. To the solution was added 9.33 grams of 3-methacryloxypropyltris(methoxyethoxy)silane and three grams of t-butyl peroctoate initiator. After fifteen minutes of purging with argon, the grafted copolymer solution in the flask was heated to eighty degrees Centigrade for five hours while maintaining the argon blanket. The flask was cooled to room temperature and contained 400 grams of the graft copolymer.

EXAMPLE II

The 400 grams of graft copolymer produced in Example I was cold blended with 600 grams of a thirty percent solution of a silsesquioxane resin in ethyl acetate. The silsesquioxane resin was a material having the formula $(PhSiO_{3/2})_x(PrSiO_{3/2})_yOH$ Ph is phenyl, Pr is propyl, and the ratio of x:y is 7:3. The blend was tested for hardness on glass in accordance with standard industry "Sward Rocker Hardness Test" which is used for measuring the hardness of organic coatings. Basically, the Rocker device consists of two flat four inch chromium plated bronze rings spaced one inch apart. Amplitudes of oscillation on a particular surface upon which it is placed are indicated by two tube style levels in the lower half of the Rocker. In the test, the swings are counted and multiplied by two to arrive at the Rocker value.

The Sward Rocker Hardness values for the blend on glass after two hours was eight, and after twenty-four hours was eleven. This is a significant improvement over Rocker values of standard nitrocellulose based nail enamels which are typically anywhere in the range of 3–7 after two hours, and from 5–12 after twenty-four hours.

EXAMPLE III

The blend of Example II was tested for adhesion on glass in accordance with the procedure of the standard industry "Cross-Cut Tape Test" set forth in the American Society for Testing and Materials designation under the standard ASTM D3359-78. In this test, cross cuts are made in the film to the substrate, pressure sensitive tape is applied over the cut and removed, and adhesion is assessed qualitatively on a scale of from zero to five, with the value five being the best. Adhesion on glass for the blend of Example II after twenty-four hours was five which is comparable for adhesion values for nitrocellulose based nail enamels.

EXAMPLE IV.

Examples I–III were repeated except that dibenzoyl peroxide was used as the free radical initiator. The same hardness and adhesion values were obtained as in the prior examples.

EXAMPLE V

Examples I–III were repeated except that butyl acetate was used as the solvent. The hardness and adhesion values were comparable to the values obtained in the prior examples.

EXAMPLE VI

Examples I–III were repeated except that 100 grams of the graft copolymer produced in Example I was cold blended with 900 grams of a thirty percent solution of a silsesquioxane resin in ethyl acetate. The silsesquioxane resin was a material having the formula $(PhSiO_{2/2})_a(MePhSiO_{2/2})_b(PhSiO_{3/2})_c(MeSiO_{3/2})_dOH$ in which Ph is phenyl, Me is methyl, and the ratio of the integers a:b:c:d is 10:5:40:45, respectively. The hardness value on glass after two hours was sixteenth and the value after twenty-four hours was thirty-four. The adhesion value on glass after twenty-four hours was five.

The following additional examples are set forth in order to illustrate in more detail the alternate embodiment of the invention.

EXAMPLE VII

Into a three neck reaction flask containing 700 grams of ethyl acetate solvent and six grams of t-butyl peroctoate free radical initiator, here was added and dissolved 126.69 grams of methyl methacrylate and 66.183 grams of butyl acrylate. The solution was purged with argon for fifteen minutes. While stirring and maintaining an argon blanket, the system was heated to sixty degrees Centigrade for one hour, and then heated to reflux at eighty degrees Centigrade for ten hours. After cooling to room temperature, there was added 9.825 grams of 3-methacryloxypropyltris(methoxyethoxy)silane and three grams of t-butylperoctoate initiator. The system was purged with argon fop fifteen minutes, an argon blanket was established, and the polymerization was allowed to proceed fop five hours at eighty degrees Centigrade. The flask was allowed to cool to room temperature. To the solution was added 97.3 grams of vinylbenzyl chloride ($H_2C=CHC_6H_4CH_2Cl$) and three grams of t-butyl peroctoate initiator. After fifteen minutes of purging with argon, the grafted copolymer solution in the flask was heated to eighty degrees Centigrade for five hours while maintaining the argon blanket. The ethyl acetate was stripped and fresh ethyl acetate was added to the flask. The flask was cooled to room temperature.

EXAMPLE VIII

The graft copolymer produced in Example VII was tested for hardness on glass in accordance with "Sward Rocker Hardness Test" in accordance with the procedure explained in Example II. The Sward Rocker Hardness values for this alternate form of graft copolymer on glass after two hours was eight, and after twenty-four hours was seventeen.

EXAMPLE IX

The graft copolymer of Example VII was tested for adhesion on glass in accordance with the procedure of the "Cross-Cut Tape Test", the details of which are explained above in Example III. Adhesion on glass for the alternate form of graft copolymer after twenty-four hours was five which is equivalent to one hundred percent adhesion. For purposes of comparison, the graft copolymers of the '268 patent were similarly tested for adhesion and exhibited an adhesion on glass after twenty-four hours of twenty percent, which in accordance with the test, is equivalent to an adhesion value of zero. The zero value norm is used to indicate anything less than sixty-five percent.

The results of Example IX clearly indicate that graft copolymers containing along the main backbone chain grafted units of vinylbenzyl chloride function remarkably better than the equivalent graft copolymers containing carboxyl units along the main backbone chain derived from acrylic acid as in the '268 patent. This improvement is quite unexpected, and is believed to be due to the fact that the active chlorine site in the grafted unit is capable of forming bonds with OH groups available on the surface of the nail. Therefore, more durable and substantive films can be formed on the nails with this type of graft copolymer. The improvement is also believed to be due to the fact that the active chlorine site in the grafted unit is capable of reacting with the amino acids typically found in human finger and toe nails, resulting again in more durable and substantive films. The amino acid composition of a fingernail, for example, is 12 percent cystine, 8.5 percent arginine, 0.5 percent histidine, 2.5 percent tyrosine, 2.6 percent lysine, 1.1 percent tryptophan; with the remainder being represented by amino acids containing alkyl chains such as glycine, alanine, leucine, and valine.

Nail enamels in accordance with the present invention can be formulated to include the grafted polymers and blends described above as the primary film forming resin. In addition to the primary film forming resin the nail enamels require a plasticizer, a solvent and a colorant.

The plasticizer functions to control the flexibility and the elongation of the film. Plasticizers preferably should be nonvolatile, colorless, odorless and tasteless. Some examples of appropriate plasticizers which may be employed are dibutyl phthalate, Ericresyl phosphate, dibutyl phthalate, dibutyl glycolate, dioctyl phthalate, camphor, castor oil, benzyl benzoate, tributyl phosphate, butyl acetal ricenoleate, glyceryl acetal ricenoleate, butyl stearate, tributoxy ethyl phosphate, triphenyl phosphate, triethyl citrate, tributyl citrate, tributyl acetyl citrate, dibutyl tartarate, dimethoxy ethyl phthalate, and diamyl phthalate.

Solvents and diluents which may be used are acetone, ethyl acetate, butyl acetate, methyl glycol acetate, methyl ethyl ketone, methyl isobutyl ketone, methyl acetate, toluene and xylene.

As a colorant there may be employed organic pigments such as The Cosmetics, Toiletries and Fragrance Association designated materials D and C Red Nos. 5-7, 10-13 and 34, and D and C Yellow Nos. 5 and 6. Cosmetic grade inorganic pigments may also be employed such as yellow and red iron oxides, brown iron oxide, iron blue, iron black, carbon black, purified titanium dioxide and bismuth oxychloride.

Nail lacquers and nail enamel formulations in accordance with the present invention contain six to thirty-five percent by weight of the primary film forming resin, five to eight percent by weight of the plasticizer, sixty to eighty percent by weight of the solvent system and about 0.05 to six percent by weight of colorant.

It will be apparent from the foregoing that many other variations and modifications may be made in the compounds, compositions and methods described herein without departing substantially from the essential features and concepts of the present invention. Accordingly it should be clearly understood that the forms of the invention described herein are exemplary only and are not intended as limitations on the scope of the present invention as defined in the appended claims.

That which is claimed is:

1. A composition comprising a blend of (i) a graft copolymer having a main backbone chain of acrylic ester units and methacrylic ester units, the main backbone chain having grafted thereto pendant trialkoxysilyl groups and pendant ethylene glycol dimethacrylate groups, the trialkoxysilyl grafts being grafted to only acrylic ester units and the ethylene glycol dimethacrylate grafts being grafted to other of the remaining unsubstituted acrylic ester units; and (ii) a silsesquioxane resin containing $RSiO_{3/2}$ units and $\equiv SiOH$ units in which R is an alkyl group or an aryl group.

2. A composition according to claim 1 in which the acrylic ester unit is formed from a precursor having the formula $CH_2=CHCOOR$ in which R is an alkyl group having from one to sixteen carbon atoms, and the methacrylic ester unit is formed from a precursor having the formula $CH_2=C(CH_3)COOR'$ in which R' is an alkyl group having one to fourteen carbon atoms.

3. A composition according to claim 2 in which the acrylic ester units are butyl acrylate and the methacrylic ester units are methyl methacrylate.

4. A composition according to claim 1 in which the trialkoxysilyl grafts are formed by reacting the main backbone chain copolymer with an acrylate or methacrylate functional silane monomer in the presence of a free radical initiator.

5. A composition according to claim 4 in which the silane monomer is 3-methacryloxypropyltris(methoxyethoxy)silane.

6. A composition according to claim 1 in which the ethylene glycol methacrylate grafts are formed by reacting the main backbone chain copolymer with ethylene glycol functional dimethacrylate monomer in the presence of a free radical initiator.

7. A composition according to claim 1 in which the blend is formed by combining 10 to 50 parts by weight of the graft copolymer in the form of an ester solvent solution containing 10 to 50 percent by weight of the graft copolymer, and 50 to 90 parts by weight of an ester solvent solution containing 10 to fifty percent by weight of the silsesquioxane resin.

8. A composition according to claim 7 in which the solvent is an ester selected from the group consisting of methyl acetate, ethyl acetate, butyl acetate, and methyl glycol acetate.

* * * * *